United States Patent

Moskal

(10) Patent No.: US 12,308,102 B2
(45) Date of Patent: May 20, 2025

(54) DRUG LIBRARY COMPILER FOR PATIENT DEVICES

(71) Applicant: Fresenius Vial SAS, Brézins (FR)

(72) Inventor: Witold Moskal, Park Ridge, IL (US)

(73) Assignee: Fresenius Vial SAS, Brézins (FR)

( * ) Notice: Subject to any disclaimer, the term of this patent is extended or adjusted under 35 U.S.C. 154(b) by 976 days.

(21) Appl. No.: 17/054,451

(22) PCT Filed: Apr. 4, 2019

(86) PCT No.: PCT/EP2019/058492
§ 371 (c)(1),
(2) Date: Nov. 10, 2020

(87) PCT Pub. No.: WO2019/219290
PCT Pub. Date: Nov. 21, 2019

(65) Prior Publication Data
US 2021/0233638 A1    Jul. 29, 2021

Related U.S. Application Data

(60) Provisional application No. 62/671,412, filed on May 14, 2018.

(51) Int. Cl.
*G16H 40/20* (2018.01)
*G16H 20/17* (2018.01)
*G16H 40/67* (2018.01)

(52) U.S. Cl.
CPC ............. *G16H 20/17* (2018.01); *G16H 40/20* (2018.01); *G16H 40/67* (2018.01)

(58) Field of Classification Search
USPC ........................................................ 700/90
See application file for complete search history.

(56) References Cited

U.S. PATENT DOCUMENTS

6,327,535 B1    12/2001 Evans et al.
8,051,414 B2    11/2011 Stender et al.
(Continued)

FOREIGN PATENT DOCUMENTS

EP    1744262    1/2007
JP    2007-140775    6/2007
(Continued)

OTHER PUBLICATIONS

Bronzino (Ed.), Chapter 9—Computer Systems of Interest To Clinical Engineers Management of Medical Technology, Butterworth-Heinemann, 1992, pp. 315-376 (Year: 1992).*
(Continued)

*Primary Examiner* — Emilio J Saavedra
(74) *Attorney, Agent, or Firm* — Cook Alex Ltd.

(57) ABSTRACT

A compiler system and method for providing a drug library to patient devices includes a memory and a processing circuit. The memory stores a drug library in a first format, the drug library comprising drug data to be used by software on the patient devices to program the patient devices to administer a drug to a patient according to a protocol determined at least in part by a user. The processing circuit configured to identify a type of patient device from prestored patient device types and select a compiler program from prestored compiler programs. The selected program is used translate the drug library from the first format into a selected second format. The translated drug library is stored in the second format and distributed to a patient device of the identified type.

19 Claims, 7 Drawing Sheets

(56) References Cited

U.S. PATENT DOCUMENTS

| | | | |
|---|---|---|---|
| 9,135,393 B1 | 9/2015 | Blomquist | |
| 2002/0083342 A1 | 6/2002 | Webb et al. | |
| 2002/0169636 A1 | 11/2002 | Eggers et al. | |
| 2004/0133876 A1* | 7/2004 | Sproule | G06Q 10/10 717/105 |
| 2005/0015236 A1* | 1/2005 | Wain | G06F 8/41 704/1 |
| 2005/0108057 A1 | 5/2005 | Cohen et al. | |
| 2005/0137653 A1 | 6/2005 | Friedman et al. | |
| 2007/0233521 A1* | 10/2007 | Wehba | G16H 20/17 700/216 |
| 2008/0126969 A1* | 5/2008 | Blomquist | A61M 5/142 715/771 |
| 2008/0233925 A1 | 9/2008 | Sun et al. | |
| 2011/0264043 A1 | 10/2011 | Kotnik et al. | |
| 2013/0006666 A1 | 1/2013 | Schneider et al. | |
| 2013/0191513 A1 | 7/2013 | Kamen et al. | |
| 2013/0221084 A1 | 8/2013 | Doss et al. | |
| 2014/0108600 A1* | 4/2014 | Cabillic | G06F 8/71 709/217 |
| 2015/0370973 A1* | 12/2015 | Jones | G16H 20/17 705/2 |
| 2017/0269907 A1* | 9/2017 | Goetz | G06F 8/30 |
| 2017/0286066 A1* | 10/2017 | Gathala | G06F 8/30 |
| 2018/0268116 A1* | 9/2018 | Deaver | G06F 21/629 |
| 2019/0294582 A1* | 9/2019 | Zhu | H04L 67/1095 |

FOREIGN PATENT DOCUMENTS

| | | | |
|---|---|---|---|
| JP | 2007-526024 | 9/2007 | |
| JP | 2008-538708 | 11/2008 | |
| JP | 2009-531146 | 9/2009 | |
| JP | 2010-507176 | 3/2010 | |
| JP | 2011-065481 | 3/2011 | |
| WO | WO 03/094090 | 11/2003 | |
| WO | WO-2005036447 A2 * | 4/2005 | ............ A61M 5/142 |
| WO | WO2005/057466 | 6/2005 | |
| WO | WO2006/108304 | 10/2006 | |
| WO | WO2007/126948 | 11/2007 | |
| WO | WO2008/057729 | 5/2008 | |
| WO | WO2012/054657 | 4/2012 | |
| WO | WO2014/131730 | 9/2014 | |

OTHER PUBLICATIONS

Siv-Lee et al., "Implementation of Wireless 'Intelligent' Pump IV Infusion Technology in a Not-for-Profit Academic Hospital Setting", Hospital Pharmacy, vol. 42, No. 9, pp. 832-840 (Sept. 1, 2007).

Swim, "Deployment of an Enterprise Wireless Infusion Pump Management System," IT Horizons 2008, pp. 29-32 (2008).

International Search Report and Written Opinion, counterpart International Appl. No. PCT/EP2019/058492 (Jul. 22, 2019) (11 pages).

* cited by examiner

DRUG LIBRARY COMPILER FOR PATIENT DEVICES

CROSS REFERENCE TO RELATED APPLICATIONS

The present application is a U.S. National Stage of PCT International Patent Application No. PCT/EP2019/058492, filed Apr. 4, 2019, which claims the benefit of U.S. Provisional Patent Application No. 62/671,412, filed May 14, 2018, both of which are hereby incorporated by reference in its their entirety. The present application is related to U.S. Provisional Patent Application No. 62/671,424, filed on May 15, 2018, which application is incorporated by reference in its entirety.

BACKGROUND

Infusion pumps are used to administer drugs and other medicaments to patients, typically in a clinical setting. An infusion pump provides a controlled amount of the medicament over time to the patient. The amount is administered pursuant to parameters entered by a clinician into the pump using a pump user interface.

Drug libraries are used on infusion pumps to provide further configuration beyond the software released by the manufacturer of the device and already operating on the device. Drug libraries can be user-configurable, for example by a pharmacist, and can include drug names, doses, limits to the upper and/or lower ranges of administration parameters, and other operating configurations or parameters. Some healthcare facilities may have several different types of patient devices. Drug libraries or other data sets are to be created, released and distributed to the different types of pumps. At times, a patient device of a new type is added to a healthcare facility and drug libraries are to be created for, released and distributed to the new type of patient device.

DETAILED DESCRIPTION OF ILLUSTRATIVE EMBODIMENTS

In some embodiments, a distribution system of data sets to patient devices is provided which is flexible and secure.

In some embodiments, a distribution server may provide the ability to compile the same drug and/or therapy data defined by a pharmacist into different formats of drug libraries serving different infusion pumps.

In some embodiments, virtually the same and common user interface can be used to produce drug libraries for vastly different pump types and families.

In some embodiments, the systems and methods described herein may simplify management of deployment environments that include a variety of infusion pumps.

In some embodiments, additional compilers for new types of infusion pumps can be readily added to the distribution system.

In some embodiments, a compiler system is configured to provide a drug library to patient devices, the compiler system comprising a memory and an electronic processing circuit. The memory may be configured to store a drug library in a first format, the drug library comprising drug data to be used by software on the patient devices to program the patient devices to administer a drug to a patient according to a protocol determined at least in part by a user.

The processing circuit may be configured to read the drug library, identify a type of patient device from a plurality of prestored patient device types, select a compiler program from a plurality of prestored compiler programs, each prestored compiler program configured to compile the drug library from the first format into a respective second format, each second format being different for each type of patient device. The processing circuit may be configured further to use the selected program to translate the drug library from the first format into a selected second format, store the translated drug library in the second format and distribute the translated drug library in the second format to a patient device of the identified type.

In some embodiments, the drug library may comprise programming parameters that provide default values and limits (hard limits and/or soft limits) to a user's ability to program the infusion pump. The drug library may comprise different sets of programming parameters for different drugs. The drug library may comprise a "drug X" data set for a drug not known by the data library.

In some embodiments, a drug library may be created in a first workspace, a release process may be done in a second workspace, and a distribution process may be done in a third workspace. In some embodiments, each workspace may comprise a file system where files of interest for a common function are located, whether it be on a single computer or across several computers. In some embodiments, each workspace may comprise defined entry and/or exit criteria for a user, such as a user account, a user credential, user characteristics, etc. In some embodiments, each workspace may comprise a respective dedicated user interface, database and/or data rule verification algorithm.

In some embodiments, a workspace separate from a drug library creating workspace may be configured to compile data libraries. The workspace for compiling may compile drug library using a pump-specific or pump-type-specific compiler program.

In some embodiments, a workspace separate from the compiler workspace or release workspace may be configured to provide a drug library editor for use by a pharmacist or other person to edit a plurality of drug libraries. The drug library editor may be configured to require user authentication before a person may access functions of the drug library editor.

In some embodiments, a release workspace separate from an editor workspace may be configured to release drug libraries in read-only format.

In some embodiments, infusion pumps in a workspace separate from the release workspace may request infusion pump data from the release workspace. Infusion pumps may then receive a dataset or updated set of infusion pump data from a server computer in the release workspace. In some embodiments, an infusion pump is configured to require user input to install or activate a new data set, for example by cycling the power on the infusion pump. In some embodiments, an infusion pump may notify the server computer in the release workspace that the new data set has been installed, upon completion of the installation. The infusion pump may be configured to disconnect from or end a communication session with the server computer after the notification.

In some embodiments, a drug library user interface may be configured to receive edits to drug libraries from a person. The drug library user interface may also receive inputs for release profiles defining which drug library is to be released to which medical device or medical devices, and when.

In some embodiments, each data set may comprise one or more of parameters, limits, configurations, values or other data for defining the operation of an infusion pump or pumps. In some embodiments, each data set is not operating software, but is a set of data used by operating software to define a function of a medical device.

In some embodiments, a distribution server may be configured to release drug libraries and also to release device configurations such as screen time-out, screen brightness, and other parameters for general use of the infusion pump across different drug libraries.

In some embodiments, a computer presents a distribution user interface to receive a distribution policy from a person. The distribution policy may define which drug libraries, configuration files, etc. are to be distributed to which infusion pumps, and optionally at which times (e.g., date/time, immediately, etc.).

In some embodiments, a method of providing a drug library to patient devices comprises storing a drug library in a first format. The drug library may comprise drug data to be used by software on the patient devices to program the patient devices to administer a drug to a patient according to a protocol determined at least in part by a user. The method may comprise reading the drug library, identifying a type of patient device from a plurality of prestored patient device types, selecting a compiler program from a plurality of prestored compiler and using the selected program to translate the drug library from the first format into a selected second format. Each prestored compiler program may be configured to compile the drug library from the first format into a respective second format, each second format being different for each type of patient device. The method may further comprise storing the translated drug library in the second format and distributing the translated drug library in the second format to a patient device of the identified type.

In some embodiments, a processing circuit is configured to convert drug library data entered by a person, such as a pharmacist, into drug library data formats required by pumps. The processing circuit may store in a memory pump-specific compiler instances, programs or data files to enable generation of drug libraries into formats of different pumps. In some embodiments, each compiler may be configured to compile a drug library for a specific type of pump or a specific family of pump (e.g., a volume-type pump, a syringe pump, a Patient Controlled Analgesia pump, etc.).

In some embodiments, a linker may comprise an execution thread component of an application server configured to link selected drug library data into a data set to targeted pump types by combining a plurality of profiles (e.g., care areas, such as neonatal intensive care unit or NICU, surgery, ambulatory care, etc.) into a single data set binary file.

In some embodiments, a compiler may comprise an execution thread component for receiving drug library parameters from a person via a first dedicated user interface of application server. The compiler may be configured to compile drug library data to target infusion pumps by verifying drug library data against defined pump drug library rules. In some embodiments, after compilation, compiled data sets may be distributed to or transmitted to patient devices over a computer network.

In some embodiments, a memory may be configured to store a drug library in a first format, such as a source code format. In some embodiments, the drug library may comprise drug data, such as drug name, hard/soft limits of user-programmable dosing parameters, bolus default values, etc.). In some embodiments, a compiler may be configured to read the stored drug library from the memory, to identify a type of patient device from a plurality of prestored patient device types, to select a compiler program from a plurality of prestored compiler programs and use the selected compiler program to translate or compile the drug library from the first format to a second format. In some embodiments, the second format can be a lower-level code format than that of the first format, such as a machine code.

In some embodiments, the type of patient device may be identified by reading a code embedded in a data library. In some embodiments, the type of patient device may be identified by receiving user input data from a user interface. In some embodiments, each second format may be different for different types of patient devices. In some embodiments, each second format may share one or more common characteristics, such as being machine code, being object code, being binary files, etc.

In some embodiments, a compiler may perform one or more of preprocessing, lexical analysis, parsing, semantic analysis, conversion of input programs to an intermediate representation, code organizing, code generation, etc.

In some embodiments, a compiler is a cross-compiler, a bootstrap compiler or a source-to-source compiler.

In some embodiments, a drug library or therapy data file may be defined by a pharmacist via a user interface and compiled into different second formats for different types of infusion pumps. In some embodiments, a compiler may be configured to translate a drug library in a source code format to a plurality of different machine code formats using different patient device-type compilers for different respective patient device types.

In some embodiments, a distribution database may be configured to store compiled data sets before distributing the compiled data sets in second formats to respective patient devices of associated types.

In some embodiments, each of the workspaces may comprise its own dedicated database and/or entry and/or exit criteria for a user.

In some embodiments, a release workspace may be configured to generate a release report based on the translated drug library and to receive a sign-off authorization via a dedicated user interface. In some embodiments, the sign-off authorization may comprise a dual sign-off requiring two persons to electronically sign off.

In some embodiments, a compiler may be configured to receive a new compiler program for a new patient device type and store the new compiler program with the plurality of prestored compiler programs.

In some embodiments, a computer system provides a drug library to infusion pumps. A compiler circuit can comprise a portion of an electronic processing circuit for operating a compiler algorithm. A memory can store a drug library in a source code format, the drug library comprising drug data to be used by software already programmed on the infusion pumps to program the infusion pumps to administer a drug to a patient according to a protocol determined at least in part by a clinician. The drug library can comprise hard and soft limits for parameters to be programmed by the clinician. Hard limits may comprise parameter limits that cannot be overridden by an end user of the medical device, while soft limits may comprise parameter limits that trigger an alert for the end user but can be overridden by the end user. In some embodiments, a processing circuit can be configured to identify a type of infusion pump from a plurality of prestored infusion pump types and select a compiler program from a plurality of prestored compiler programs based on the identified type of infusion pump. Each prestored compiler program can be configured to compile the drug library from the source code format into a respective machine code format, each machine code format being different for each type of infusion pump. In some embodiments, the processing circuit can use the selected program to translate the drug library from the source code format into the selected machine code format and to store and distribute the translated drug library in the machine code format to a patient device of the identified type.

Some embodiments may comprise a drug library editor circuit comprising a first dedicated user interface configured to receive drug library parameters from a pharmacist.

Some embodiments may comprise a release circuit comprising a second dedicated user interface configured to release the translated drug library in the second format to the infusion pump of the identified type.

In some embodiments, if the patient device type that was identified and/or read from the drug library is not in the types of patient devices stored in memory, the user may be prompted to load a new compiler. In some embodiments, a notification may be provided to a user to download the compiler from a website link.

Figure 1:
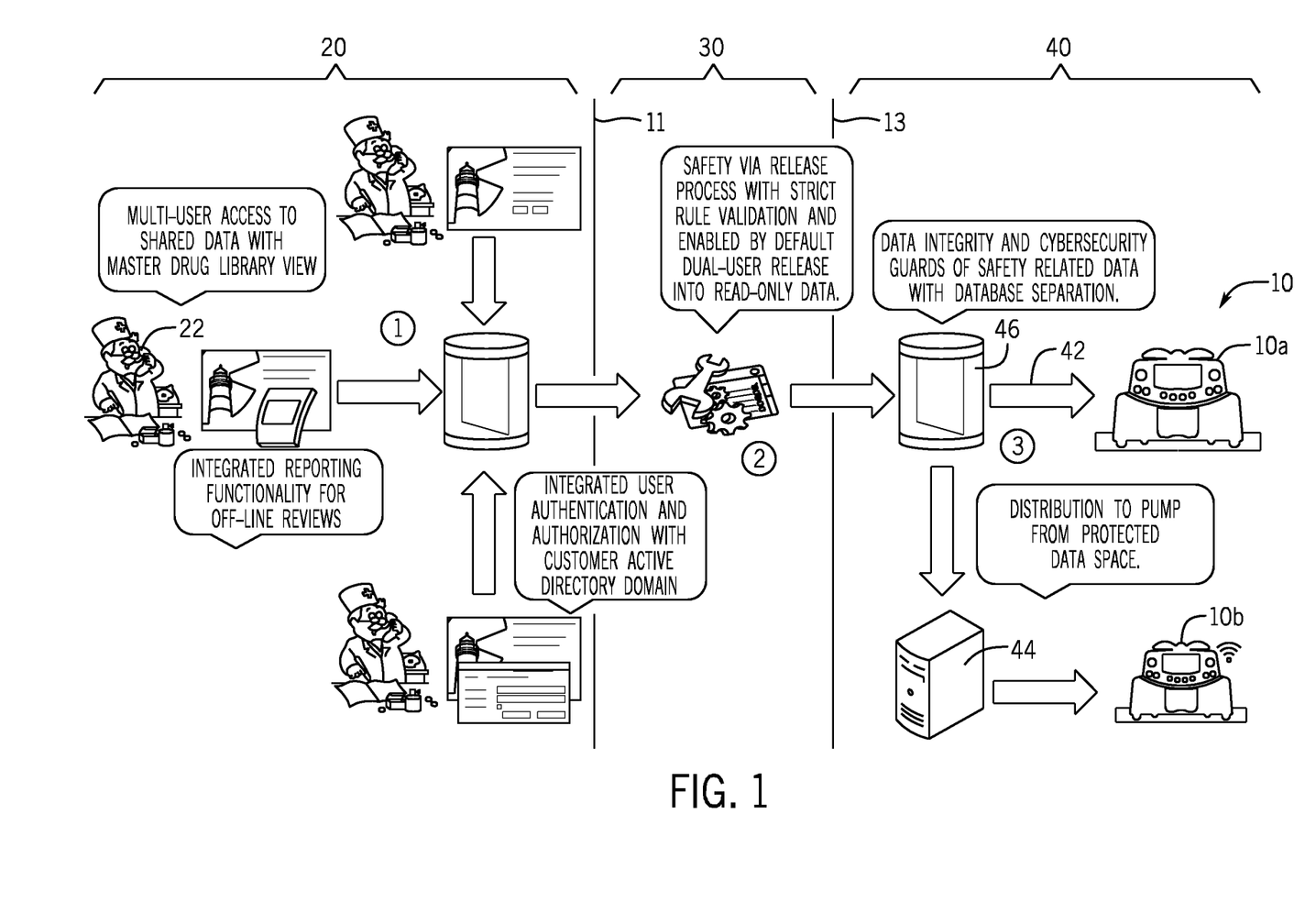
FIG. 1 is a functional diagram of a product architecture for a drug library distribution system for patient devices, according to an illustrative embodiment.

Referring now to FIG. 1, a flow diagram of a system for programming a patient device with a dataset from a server computer will be described. In this example, the patient device is an infusion pump 10 of a first type 10a or second type 10b, though in alternative embodiments the patient device may be any medical device, such as any device configured to provide medical functions or services to a patient (including a blood or organ donor) in any clinical, hospital, home care, or other setting, by way of invasive procedure (e.g., using a needle in a procedure) or otherwise. Infusion pump 10 may be any of a variety of infusion pumps, such as a large volume infusion pump (i.e. one configured to dispense from a bag instead of a syringe), a patient-controlled analgesia (PCA) pump, elastomeric pump, syringe pump, enteral or parenteral feeding pump, insulin pump, etc. At Step 1 in FIG. 1, a user (e.g., a pharmacist, biomedical engineer, etc.) logs into a server computer or terminal (e.g., pharmacy computer located or disposed in a pharmacy to be programmed by a pharmacist) in communication with the server computer. The user creates, edits, and/or selects one or more datasets to be programmed into or downloaded to infusion pump(s) 10 to satisfy needs of an end user workflow in the deployment environment (e.g., hospitals, health care facilities, clinics, etc.). The dataset may comprise data that the infusion pump uses in its operation. For example, the dataset may be a library of drug programming parameters that provide default values and limits to a user's ability to program the infusion pump. For example, a data set may comprise hard limits and/or soft limits to different pump programming parameters, such as infusion rate, dose, infusion time or duration, etc. The limits of the data set may be different for different drugs, and may include a "drug X" data set for a drug not known by the data library. Once changes are made to the data set or library, the server computer may be used to release (Step 2) and distribute (Step 3) data sets to configure, update and/or otherwise program infusion pumps 10, which may be done individually, by care area, universally, etc., with the new data set created by the pharmacist or other user. The user may select a date and time after which the infusion pump will receive the new dataset. The patient devices may be clinician-programmable infusion pumps, wherein the data set comprises hard and soft limits for parameters to be programmed by a clinician.

In the illustrative embodiment of FIG. 1, the architecture separates each of workflow steps 1, 2 and 3 via independently defined data and processing concepts to provide desired value-added functionality. As indicated graphically by lines 11 and 13, creating drug libraries (Step 1) may be done in a separate data workspace from the workspace of a release process (Step 2), both of which are separate workspaces from a distribution process (Step 3). A workspace may refer to a file system where files of interest for a common function are located, whether it be on a single computer or across several computers. In some embodiments, a workspace may further comprise a dedicated database (again virtually with other dedicated databases on a single computer, on separate computers, on a server farm, in a cloud computing environment in which computers share tasks, etc.). In some embodiments, a workspace may further comprise defined entry and/or exit criteria for a user, such as, a user account, user credentials, user characteristics, user qualifications, etc. In the embodiment of FIG. 1, each of drug library editor workspace 20, release workspace 30 and distribution workspace 40 may require dedicated entry and/or exit criteria for users. Each workspace may further be configured to produce defined output data based on provided input data. Each of the workspaces or stages of the user workflow described in FIG. 1 may be supported by a dedicated user interface, a database, and/or data rule verification process to ensure that a product drug library that is deployed to supported pumps is done so in a secure, effective and efficient manner.

In one example, drug library editor workspace 20 may be configured to generate or receive a drug library created by a pharmacist 22. Workspace 20 may require pharmacist 22 to enter required drug and/or therapy information. Workspace 20 may be configured to produce one or more drug library data structures that can then be passed on to the release workspace 30 of the user workflow. In this embodiment, release workspace 30 may be configured to compile the drug library data, for example using a pump-specific or pump-type-specific compiler program. Distribution workspace 40 may be configured to receive the compiled drug library data and distribute the drug library or libraries to pumps 10. Distribution may occur with a direct interface 42 to a single pump at a time (for example via a programming computer with a Universal Serial Bus interface, Ethernet interface, Wi-Fi interface, Bluetooth interface, etc.) and/or indirectly and simultaneously to a plurality of infusion pumps 10 via a distribution mechanism provided by a distribution server 44.

In some embodiments, data library editor workspace 20 may provide multi-user access to shared data with a master drug library view. In some embodiments, workspace 20 may be configured to provide reports for off-line reviews, for example via printing, saving data to memory, and/or transmitting data to another computing device. In some embodiments, workspace 20 may be configured to require user authentication and/or authorization, which may be done using a directory service, such as Active Directory domain, before a pharmacist or other user may access one or more functions of the workspace.

In some embodiments, release workspace 30 may provide a release process requiring strict rule validation. The release workspace may further be enabled by a default dual-user release requirement and may further release data files in read-only format.

At Step 3, infusion pump 10 may be configured for wired and/or wireless communication with a server computer 44. Each of pump 10 and server computer 44 may comprise a network interface circuit configured for network communications. Pump 10 is configured to transmit and server 44 is configured to receive a request for infusion pump data, such as a data set, such as a drug library of infusion data. Infusion pump data requests may be initiated by infusion pump 10 and may occur periodically, intermittently, occasionally, every few minutes, several times per day, or at other regular or irregular frequencies. Pump 10 may be configured to request whether a newer version of a dataset is available for download from server computer 44 and to download the dataset. The downloaded dataset may be stored in non-volatile storage memory. Pump 10 may be configured to display a notification (e.g., an icon or other notification) that a new dataset is downloaded and available to be programmed.

A nurse, biomedical engineering staff, or other user may, upon seeing the notification, cycle the power on the pump to install or activate the new dataset. Pump 10 may be configured to confirm via a notification that a dataset is available for upgrading or updating. Once the dataset is upgraded, pump 10 may notify server computer 44 of upgrade status (e.g., upgrade complete or successful, upgrade failed or error, etc.). Pump 10 may then disconnect from communications with server computer 44 for security purposes. After cycling the power, the nurse is able to infuse under control of the new dataset downloaded. Please replace the paragraph beginning at page 10, line 4 with the following amended paragraph:

Server computer 44 may be configured to store the upgrade status received from pump 10, log the transaction time stamp (e.g., the time the pump was upgraded, the time the upgrade confirm message was received, or other time), and generate on demand or periodically a distribution report notification to another user, such as a biomedical engineering staff member. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, etc.).

A dedicated database 46 stores compiled data sets in a secure manner, using cybersecurity protections, firewalls or other guards of safety-related data. Data integrity measures may also be employed at database 46. Further, as described above, database 46 may be provided in a separate workspace from workspaces 30 and 20 for additional security and integrity.

Figure 2:
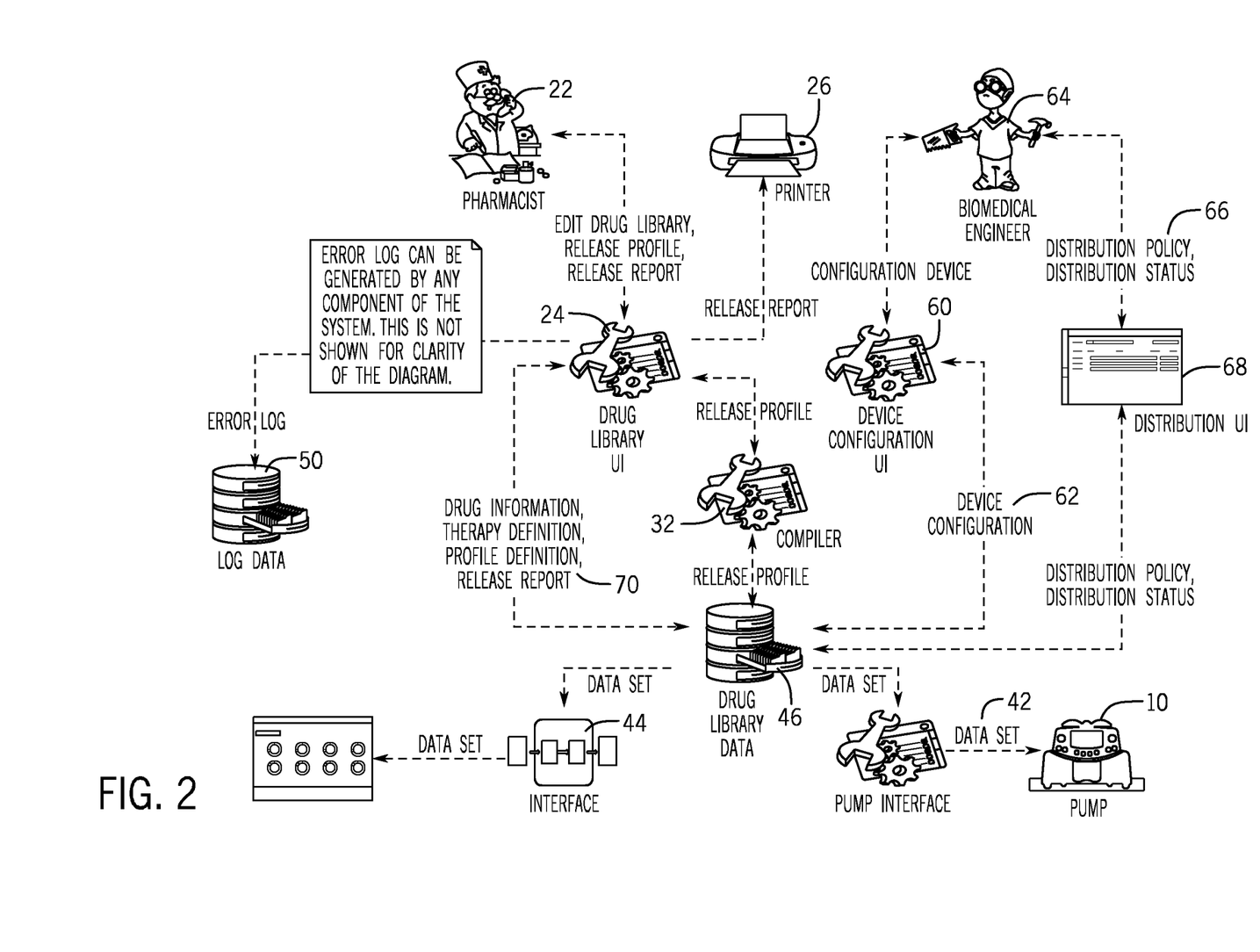
FIG. 2 is a block diagram of a product architecture for a drug library distribution system for patient devices, according to an illustrative embodiment.

Referring now to FIG. 2, a block diagram of a product architecture for a drug library distribution system for patient devices will be described. FIG. 2 contains functional components implementing features described above with reference to FIG. 1. The block diagram illustrates user interfaces, databases, applications/utilities and interfaces to external systems/devices. The various components of the architecture may be implemented by one or more computing devices. As in FIG. 1, a pharmacist 22 uses a drug library user interface 24 to edit drug libraries and display release profiles and release reports for review by the pharmacist. The release profile may be shared between controller 32 (for example, as part of release workspace 30) and drug library user interface 24. Release reports may be provided to other external devices, such as a printer 26. Error logs may be generated and stored in an error log memory 50 by any component of the system shown.

Compiled drug libraries may be released to distribution server 46 for communication to pumps 10 via a direct pump interface 42 or via a server computer 44.

Distributed data sets may comprise parameters, limits, configurations, values, or other data to be used by software 60 on the patient devices 10 to perform patient-related functions (e.g., treatment, blood component collection, etc.). In some embodiments, data sets are not operating software, but instead are used by operating software on pump 10 to determine options a user may have for programming patient device 10. As mentioned, a data set may comprise a drug library having drug names and hard and/or soft limits for drugs to be infused, the limits being determined by a pharmacist. In some embodiments, a data set is configurable by an end user, such as a pharmacist, whereas software is not user-configurable but instead is configurable only by a manufacturer or server of patient device 10.

A biomedical engineer 64 may make use of a dedicated device configuration user interface 60 to configure a device with parameters that are not drug-related, such as screen time-out, screen brightness, etc. Device configurations 62 may be released to database 46 for distribution to one or more pumps according to a distribution policy. Biomedical engineer 64 may further define a distribution policy 66 using a distribution user interface 68 and share the distribution policy with database 46 to direct the distribution of data sets to patient devices. Notably, neither the device configuration data nor the distribution policy need be controlled by controller 32 in this embodiment, though in alternative embodiments, release functions such as compiling may be applied to these data elements as well. Distribution status may be reported back from database 46 to biomedical engineer 64 using distribution user interface 68.

A release report 70 may be provided by database 46 to drug library user interface 24 to report to pharmacist or other users the statuses of data sets to be released.

Figure 3:
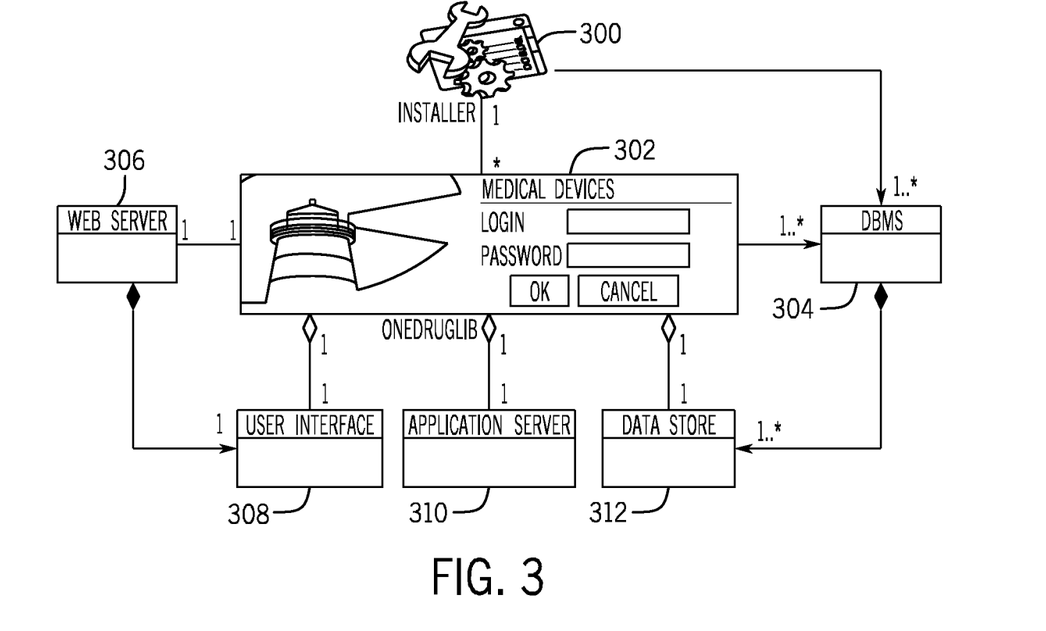
FIG. 3 is a block diagram illustrating components of a drug library distribution system for patient devices, according to an illustrative embodiment.

Referring now to FIG. 3, a block diagram of components in a data distribution system will be described. One or more of the components of the data distribution system may comprise executable computer instructions embodied on a tangible medium, such as a compact disc, digital versatile disc, memory, or other medium. An installer program 300 is provided to install the data distribution system on a computer for servicing a healthcare facility. A user interface 302 is provided which asks for login credentials of a user and facilitates other user inputs and displayed data. A commercially-available database management system 304 is provided in communication with the computer operating the data distribution system for hosting one or more data stores needed by the system. A web server 306 may be provided, also commercially-available, which may be configured to host one or more system user interfaces generated by the data distribution system.

The data distribution system embodiment on the memory comprises a user interface component 308 which generates and maintains one or more of the user interfaces described herein. An application server component 310 will be described in greater detail with reference to FIG. 4. A data store component 312 may be configured to operate database, memory, or other data storage requirements of the data distribution system, which may be implemented using DBMS 304.

Figure 4:
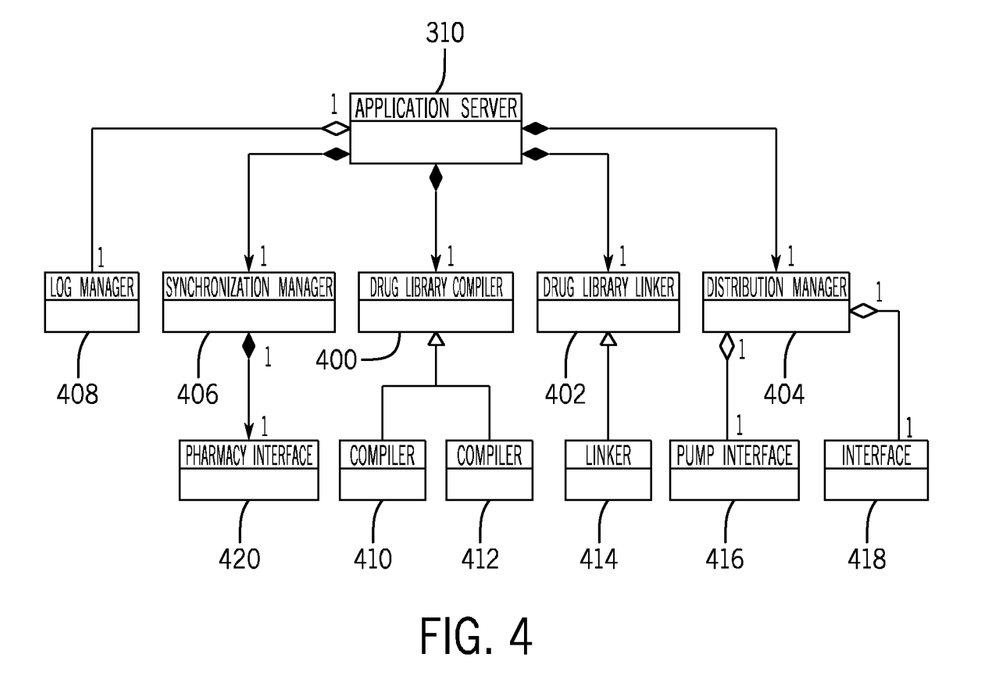
FIG. 4 is a block diagram of an application server, according to an illustrative embodiment.

Referring now to FIG. 4, a block diagram of an application server architecture will be described. Application server 310 may comprise a drug library compiler 400, a drug library linker 402, a distribution manager 404, a synchronization manager 406 and a log manager 408. Drug library compiler 400 may operate using a specific compiler version 410, 412 for each of a plurality of supported pumps. Drug library linker 402 may include a pump specific linker 414 for a particular type of pump. Some types of pumps will not have a drug library linker. Distribution manager 404 may comprise an interface 416 for a pump and an interface 418 for a separate distribution server for distribution of data sets to pumps. Synchronization manager 406 may include a hospital pharmacy system pharmacy interface 420. Log manager may manage the logging of data from one or more components of the system.

Figure 5:
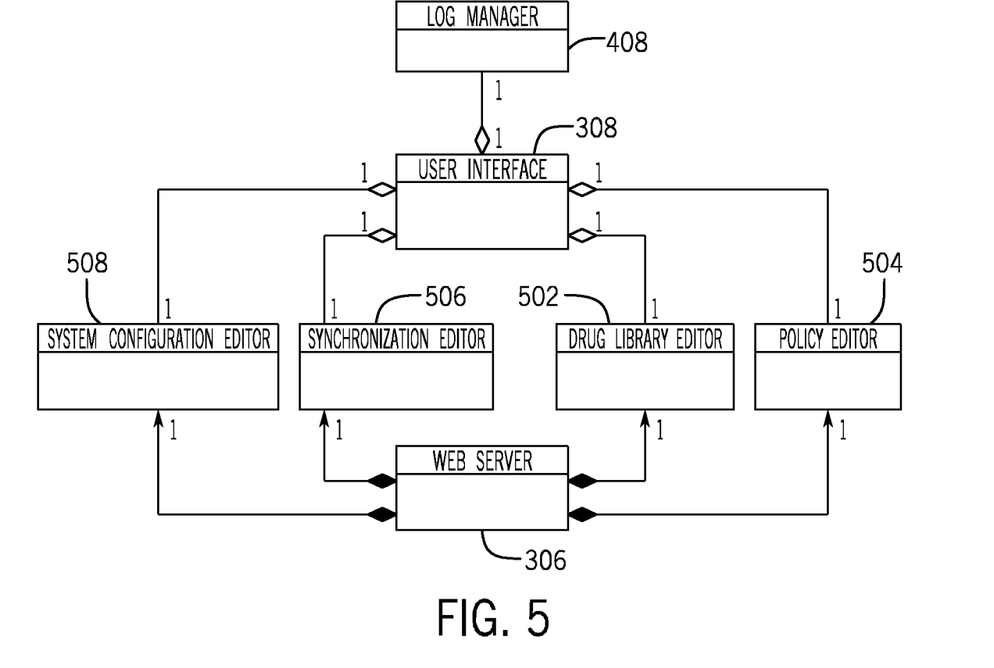
FIG. 5 is a block diagram of a system architecture for user interfaces, according to an illustrative embodiment.

Referring now to FIG. 5, a block diagram of a user interface system architecture will be described. User interface 308 may comprise a plurality of separate, dedicated interfaces, each of which may have their own log-on credentials, entry and/or exit criteria, user lists, user criteria, etc. A drug library editor 502 allows a pharmacist or other qualified user to create and edit drug libraries. A policy editor 504 allows a pharmacist or other qualified user to generate a distribution policy for a healthcare facility or medical clinic. A distribution policy may specify where and/or how the data from data files is to be distributed (e.g., to all pumps at all locations, to pumps at a specific location, to specific pump(s), etc.). A synchronization editor 506 provides synchronization of data between the data distribution system and the pharmacy interface. Each of the editors 502, 504, 506, 508 may be accessed via user interface 308 and/or web server 306. An editor refers to any program capable of editing files, such a text file editor. Log manager 408 may further be accessed by user interface 308 for the purpose of reviewing data log files retrieved from any of the components described herein.

Figure 6:
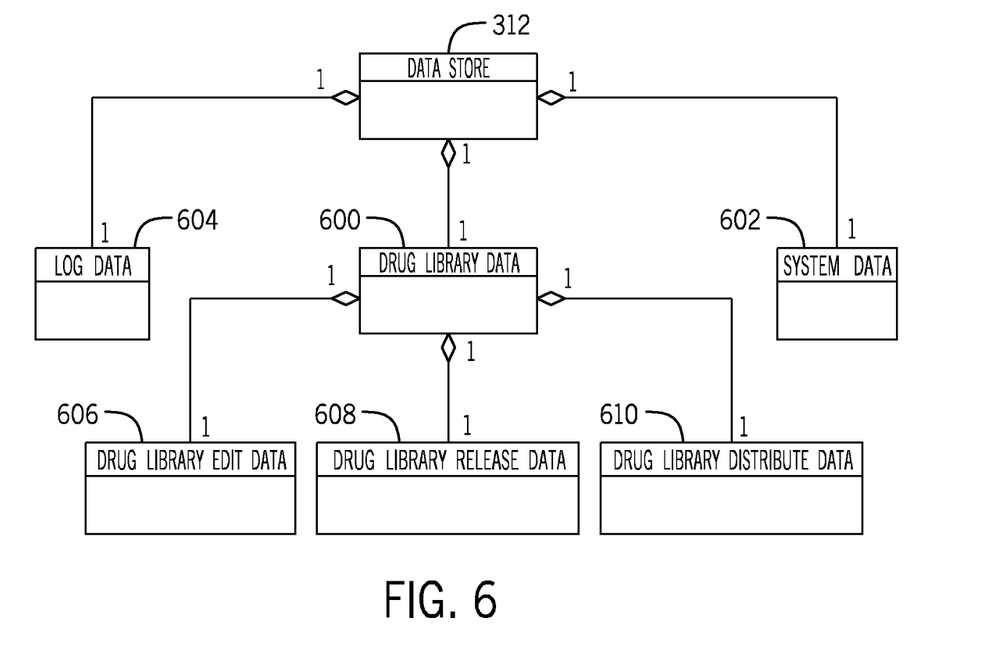
FIG. 6 is a block diagram of a system architecture for databases, according to an illustrative embodiment.

FIG. 6 is a block diagram of a data store model system architecture, according to one embodiment. Data store 312 comprises three databases in this embodiment: a drug library database 600, a system data database 602, and a log data database 604. Drug library data database 600 may include three major data schemas: drug library edit data 606, drug library release data 608 and drug library distribute data 610. DBMS 304 (FIG. 3) is deployed and managed by a drug library administrator. In some embodiments, the system will require DBMS 304 to be installed prior to installer 300 deploying the drug library distribution system.

Figure 7:
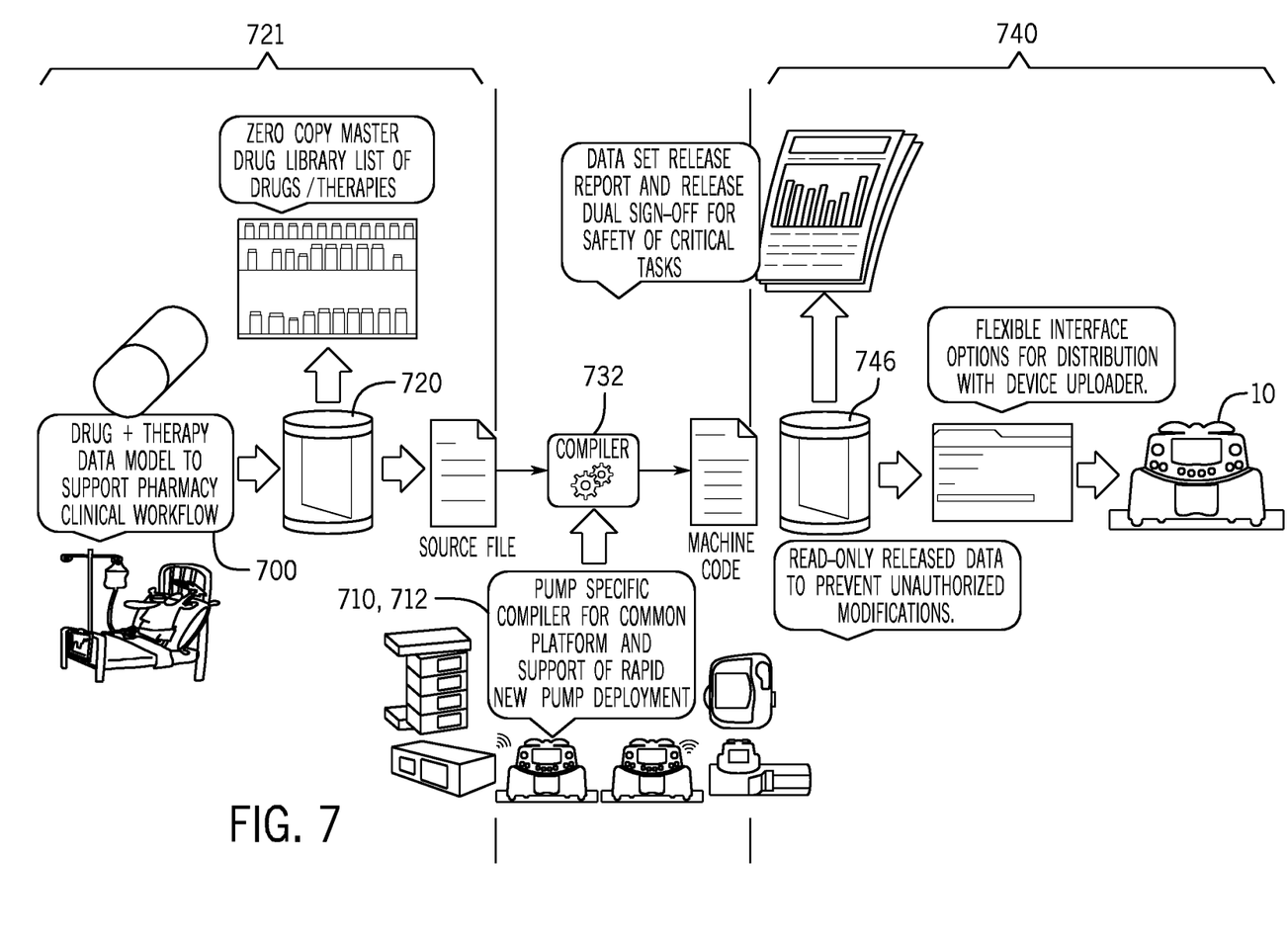
FIG. 7 is a functional diagram of a system architecture for a drug library distribution system for patient devices, showing a compiler, according to an illustrative embodiment.

Referring now to FIG. 7, a functional diagram of a system architecture for a drug library distribution system including a compiler will be described. Compiler 732 may be embodied as a programmed processing circuit configured to perform certain functions. Processing circuit 732 is a component of ODL required to provide functionality to convert drug library data entered by a pharmacist into drug library data format(s) required by supported pumps. Processing circuit 732 may include pump-specific compiler instances to enable generation of drug libraries into formats of different pumps. Each compiler may be developed to support a specific pump type and/or family, such as a volume-type pump, a PCA pump, etc. A drug library editor 24 (FIG. 2) may be a user interface component to provide a pharmacist with editing functionality of common drug library data. A drug library linker 402 (FIG. 4) may be a component for linking released drug libraries into pump supported formats. Linker 402 may comprise an execution thread component of the application server configured to link selected drug libraries data into a data set to target pump types by combining a plurality of profiles (e.g., care areas, such as neonatal intensive care unit or NICU, surgery, ambulatory care, etc.) into a single data set binary file.

In some embodiments, compiler processing circuit 732 may be an execution thread component of application server 310 (FIG. 3) configured to compile drug library data to target infusion pumps by verifying drug library data against defined pump drug library rules. One or more data sets (e.g., drug libraries) 700 may be distributed to one or more patient devices (e.g., infusion pumps) 10. A memory 720 may be configured to store a drug library in a first format, such as a source code format. Drug library 700 may comprise drug data (e.g., drug name, hard/soft limits of user-programmable dosing parameters, etc.) to be used by software on the patient devices 10 to program the patient devices 10 to administer a drug to a patient according to a protocol determined at least in part by a user. For example, a user may program an infusion pump to deliver amoxicillin at a protocol comprising a set rate and time, wherein the parameters of the protocol are limited by the drug library. Memory 720 may comprise a database which may be distinct from other databases of the system, such as distribution database 746. Databases 720, 746, etc. may be configured as relational databases or other databases.

Processing circuit 732 may be configured to read drug library 700 from memory 720 or otherwise receive it. Processing circuit 732 may be configured to identify a type of patient device from a plurality of prestored patient device types. Prestored patient device types may be stored in a memory local to or otherwise accessible to processing circuit 732. The type of patient device may be any of a plurality of types, such as a syringe pump type, a volume pump type, a PCA pump type, a specific model of one of these pump types, or other pump types. The type of patient device may be identified in any number of ways, for example, by reading a portion of or a code embedded in data library 700, by receiving the type of patient device from one of the user interfaces described herein, etc.

Processing circuit may be configured to select a compiler program from a plurality of prestored compiler programs 710, 712 and to use the selected program to translate the drug library from the first format into a selected second format. Each pump type may have a different respective and/or associated compiler program, for example pump version 1.0 compiler 710, pump version 2.0 compiler 712, etc. Each prestored compiler program 710, 712, etc. may be configured to compile the drug library 700 from the first format into a respective second format, each second format being different for each type of patient device. For example, drug library 700 may be in a source code format and compilers 710, 712 may translate the source code format into a lower-level code format such as a machine code format compatible with pump version 1.0 and a second machine code format compatible with pump version 2.0, respectively. Note that while the second formats are different for each pump, they may nevertheless share common characteristics, such as being machine code, object code, binary files, etc. In some embodiments, the first format can comprise a source code format and the second translated format can comprise an assembly code format. Other translations besides compilers are contemplated. Compilers may perform one or more of preprocessing, lexical analysis, parsing, semantic analysis, conversion of input programs to an intermediate representation, code optimization, code generation, etc. Compilers may further comprise any type of compiler, such as cross-compiler, a bootstrap compiler, a source-to-source compiler, etc.

In some embodiments, the same drug and/or therapy data defined by a pharmacist may be compiled into different formats of drug libraries serving different infusion pumps. One advantage of this structure is that it enables the product to retain virtually the same and common user interface to produce a drug library for very different pump types and families, therefore simplifying management of deployment environments that include a variety of infusion pumps. Processing circuit 732 may be configured to translate the drug library in a source code format to a plurality of different machine code formats using different patient device-type compilers for different respective patient device types.

Processing circuit 732 may be configured to store the translated drug library in the second format, which may be stored in a distribution database 746. Distribution database 746 may be configured to distribute the drug library in the second format to a patient device of the identified type.

Distinct workspaces, as described with reference to FIG. 1, may be implemented with the drug library distribution system shown in FIG. 7. For example, a drug library editor workspace 721 comprising a first dedicated user interface 24 (FIG. 2) or 502 (FIG. 5) may be configured to receive drug library parameters 700 from a pharmacist 22 (FIG. 1). A release workspace 740 comprising a second dedicated user interface 68 (FIG. 2) or 504 (FIG. 5) may be configured to release the translated drug library in the second format to the patient device 10. Further, the drug library creation workspace 721 may comprise a first dedicated database 720 and first defined entry and exit criteria for a user, such as log-in credentials, authorization checks, user authentication, etc. Similarly, the release workspace 740 may comprise a second dedicated database 746 and second defined entry and exit criteria for a user.

In some embodiments, release workspace 740 may be configured to generate a release report based on the translated drug library and to receive a sign-off authorization via the second dedicated user interface from the user. The sign-off authorization may be a dual sign-off (i.e. two persons must electronically sign off) for safety of critical tasks before a data set is released to a pump 10. Requiring dual sign-off can improve the security of the system at a key stage of the data set distribution process. In another embodiment, the release workspace 740 is configured to store and release the authorized translated drug library in a read-only format. Releasing the data in a read-only format may prevent cyber attacks and other errant meddling with the data set once it is stored in release database 746.

In some embodiments, processing circuit 732 may be configured to receive a new compiler program for a new patient device type (for example, a new pump product release, new version, new pump type, etc.) and to store the new compiler program with the plurality of prestored compiler programs. New compilers for new pump types can be added to the system at will, simplifying the rollout of a new pump.

Figure 9:
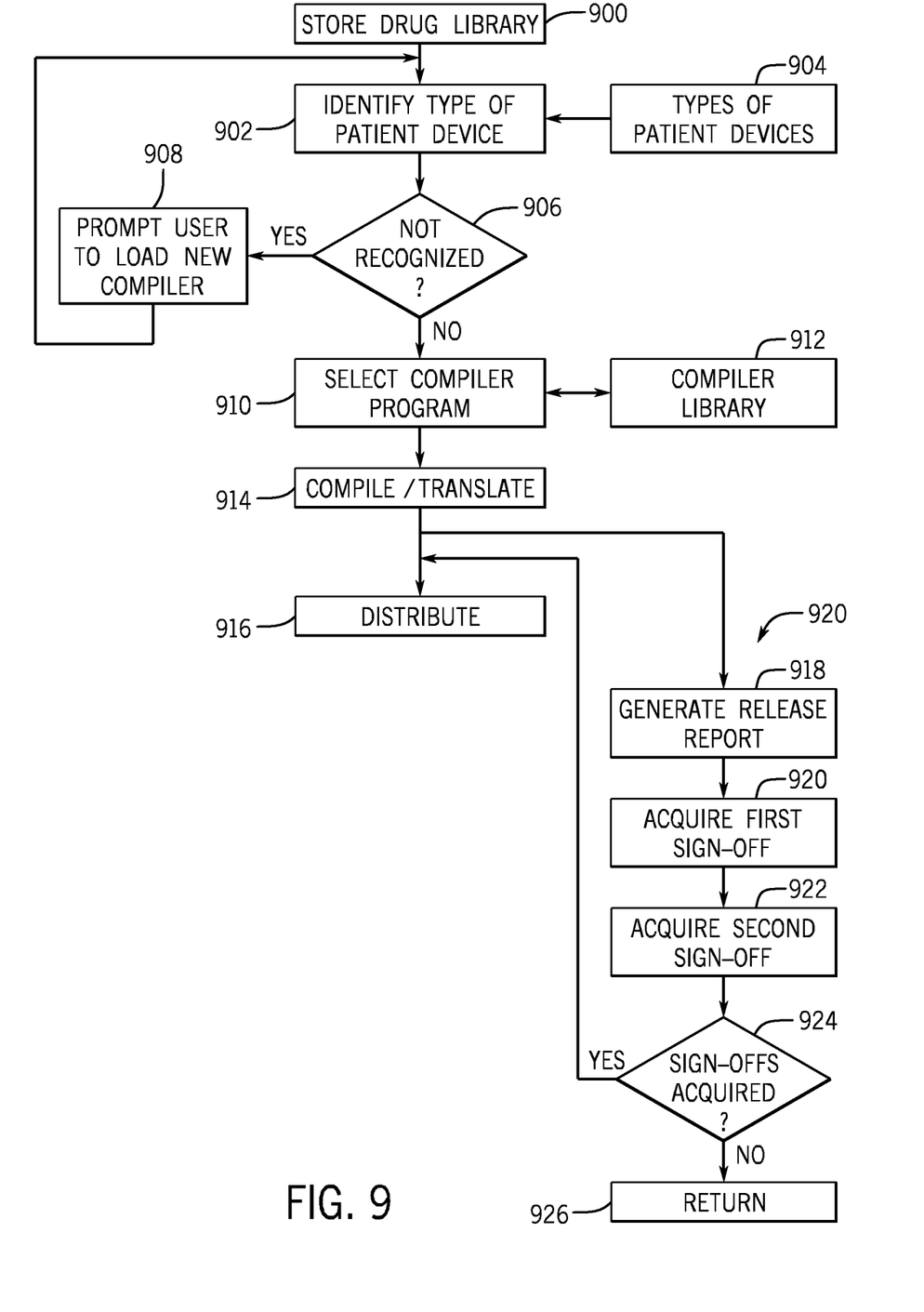
FIG. 9 is a flowchart of a method for compiling a drug library for distribution to infusion pumps, according to an illustrative embodiment.

Referring now to FIG. 9, a method of providing a drug library to patient devices will be described. At a block 900, the method comprises storing a drug library in a first format. The drug library may comprise drug data to be used by software on the patient devices to program the patient devices to administer a drug to a patient according to a protocol determined at least in part by a user. At a block 902 the drug library is read and a type of patient device is identified from a plurality of prestored patient device types 904. If the patient device type that was identified and/or read from the drug library is not in the types of patient devices (block 906), the user may be prompted to load a new compiler at block 908. Other notifications may be provided, such as a message to contact a manufacturer of the pump type identified to acquire the compiler, a link to a website to download the compiler, etc.

At a block 910, if the device type is recognized, a compiler program is selected from a plurality of prestored compiler programs (912). Each prestored compiler program is configured to compile the drug library from a first format into a respective second format, each second format having differences for each type of patient device. Compiler programs may be one-to-one compiler programs that translate a file from a first format to a second format. At block 914 the drug library is compiled or translated using the compiler program. At block 916, the translated drug library is stored and distributed to a pump, for example according to a predetermined distribution policy generated by a pharmacist or other person.

Optional additional steps 920 are shown. After block 914, at a block 918 a release report may be generated and provided to a computer, terminal or other user interface for approval by the appropriate clinical personnel. At a block 920, the method seeks to acquire a first sign-off from clinical personnel, which may be done by way of an electronic signature or other indication of approval from a properly credentialed person. At a block 922, a second sign-off is sought from a second clinical person. At block 924, if both sign-offs are not acquired, the processing exits at block 926 without distributing the drug library. If both sign-offs are acquired, processing proceeds to block 916 for distribution.

Figure 8:
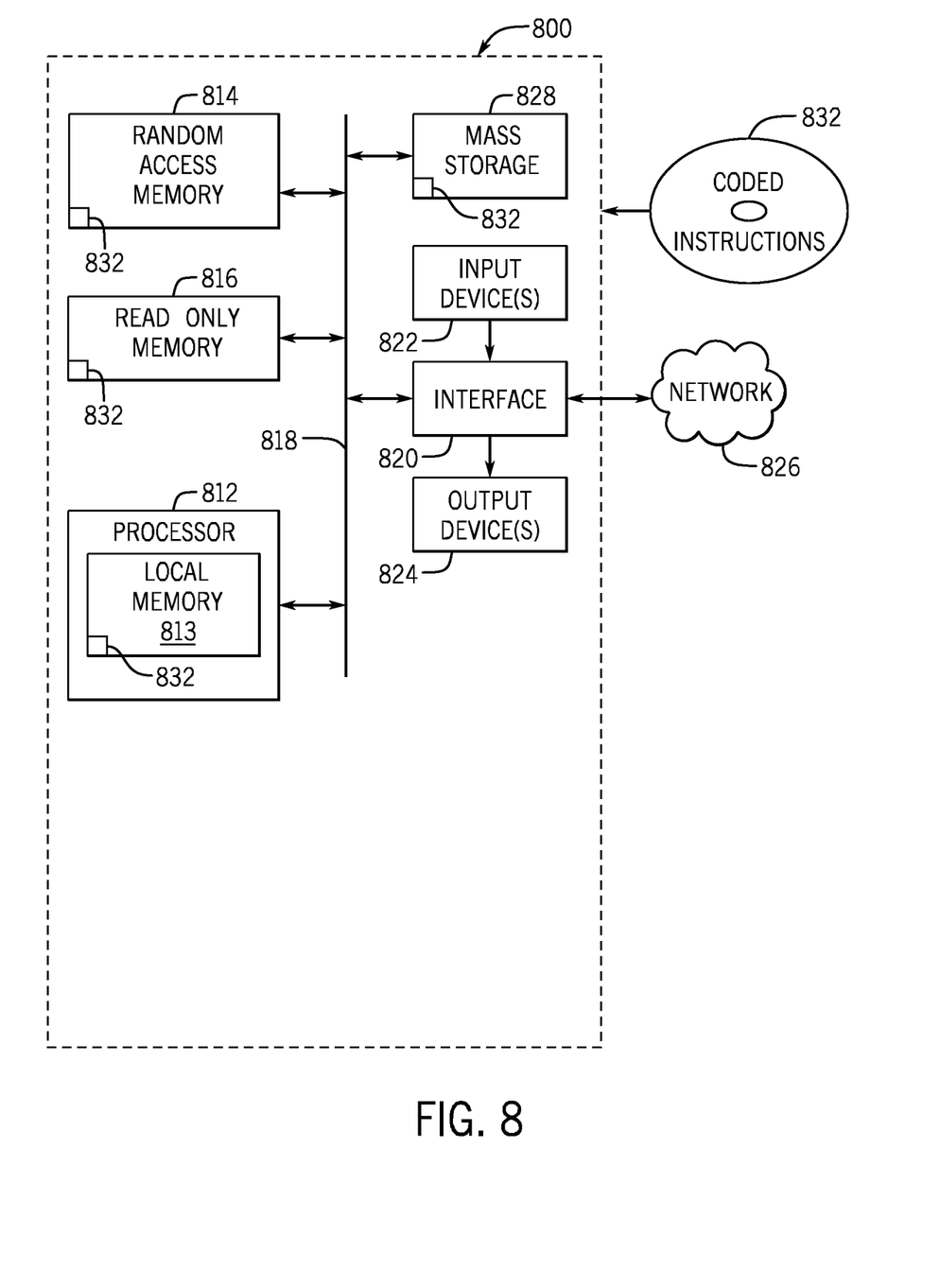
FIG. 8 is a block diagram of a processing circuit, one or more components of which may be used in the computers or other processing components described herein.

FIG. 8 is a block diagram of processing circuit components, one or more of which may be used in the computing devices described herein (e.g., server computer, pharmacy computer, patient device, uploader computer, etc.). In alternate embodiments, the systems and methods described herein may be implemented on a single server computer, a plurality of server computers, a server farm, a cloud server environment, or using other computer resources. Server 44 and patient device 10 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, and/or other circuit components. Server 44 and patient device 10 may each comprise a network interface circuit configured to provide communications over one or more networks with each other and/or with other devices. Network interface circuits among devices may comprise digital and/or analog circuit components configured to perform network communications functions. The networks may comprise one or more of a wide variety of networks, such as wired or wireless networks, wide-area, local-area or personal-area networks, proprietary or standards-based networks, etc. The networks may comprise networks such as an Ethernet network, networks operated according to Bluetooth protocols, IEEE 802.1 1× protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

FIG. 8 is a block diagram of an example processor platform 800 capable of executing the instructions described herein and/or to implement the example systems described herein. The processor platform 800 can be, for example, a server, a personal computer, a mobile device (e.g., a cell phone, a smart phone, a tablet such as an iPad™), a personal digital assistant (PDA), an Internet appliance, or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer. In the illustrated example, the processor 812 is structured to be programmed with components to implement the functions described herein, such as those applying criteria to software version indicators.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 of the illustrated example also includes an interface circuit 820. The interface circuit 820 may be implemented by any type of interface standard, such as those described hereinabove.

In the illustrated example, one or more input devices 822 are connected to the interface circuit 820. The input device(s) 822 permit(s) a user to enter data and commands into the processor 812. The input device(s) can be implemented by, for example, an audio sensor, a microphone, a camera (still or video), a keyboard, a button, a mouse, a touchscreen, a track-pad, a trackball and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

Coded instructions 832 representing the flow diagram of FIG. 9 or other steps described herein may be stored in the mass storage device 828, in the volatile memory 814, in the non-volatile memory 816, and/or on a removable tangible computer readable storage medium such as a CD or DVD.

Certain embodiments contemplate methods, systems and computer program products on any tangible machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system. Tangible computer readable media include a memory, DVD, CD, etc. storing the software and/or firmware, but do not include a propagating signal.

Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the exemplary embodiments have been described with reference to an infusion pump, the teachings herein may be applied to other medical devices, such as apheresis devices (e.g., plasmapheresis, blood therapy, etc.) or other devices that are invasive or noninvasive, that interface with a human patient via a needle in the patient's skin, insulin pumps (e.g., internal or external to the body cavity), medical imaging devices (e.g., CT scanners, x-ray imagers, magnetic resonance imaging). The teachings may also be applied outside the medical field to any computing devices, such as mobile phones, tablet computers or other computers configured to be operated while held in a human hand, laptops, personal computers, and other networked computers.

Certain examples facilitate management of medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) provides input to patient devices regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

Certain examples determine and/or update a data set distribution policy associated with a medical device data management system. If a data set distribution policy has been created, then a new or updated data set (e.g., a new or updated drug library) can be distributed to one or more medical devices, even if one or more of the target medical devices are currently operating (e.g., pump(s) are currently infusing drug into a patient). Thus, data set distribution does not impact the pump's activity.

In certain examples, a data set defines a drug library and/or instruction set for a medical device such as a "smart" infusion pump, apheresis device, etc. For example, "smart" infusion pumps utilize a drug library or other close error reduction software to perform functions that assist healthcare providers with programming and calculating drug dose and delivery rates. The drug library is a database or data set that stores drug dosing information, including dosing limits, concentration, infusion parameters, and drug specific advisories, for example. Drug library instructions can help reduce or prevent medication errors and associated patient harm, for example.

Distribution of a data set to medical devices can occur directly at the device and/or remotely over a network (e.g., from a data management system to multiple medical devices, etc.).

In certain examples, a pharmacy controls the data set and distribution, and the end user (e.g., nurse, technician, etc.) is not given decision-making authority but must accept the data set to continue using the device. The device management system sends out a data set, and a receiving device is configured to activate the new data set on next reboot. The downloaded data set is held in a download buffer, for example, and, once the device is powered on, the device programs the data set into active memory. The user is then informed of the new data set and instructed to use the device or turn the device off but cannot revert to a prior version of the data set.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

The invention claimed is:

1. A compiler system for providing a drug library to patient devices, comprising:
   a memory configured to store a drug library in a first format, the drug library comprising drug data to be used by software on the patient devices to program the patient devices to administer a drug to a patient according to a protocol determined at least in part by a user; and
   a processing circuit disposed within a healthcare facility and configured to:
   read the drug library;
   identify a type of patient device from a plurality of locally prestored patient device types and prompt the user to load a new compiler program when a patient device type is not recognized among the plurality of locally prestored patient device types;
   receive the new compiler program for a new patient device type and store the new compiler program with a plurality of locally prestored compiler programs;
   select a compiler program from the plurality of locally prestored compiler programs, each locally prestored compiler program configured to compile the drug library from the first format into a respective second format, each second format being different for each type of patient device;
   use the compiler program selected to translate the drug library from the first format into a selected second format;
   store the drug library in the selected second format; and
   distribute the drug library in the selected second format to a patient device of the type identified.

2. The compiler system of claim 1, wherein the first format is a source code format and the selected second format is a code format having a lower level than the source code format.

3. The compiler system of claim 1, wherein the patient device of the type identified is an infusion pump selected from the group comprising a syringe infusion pump and a volume-type infusion pump.

4. The compiler system of claim 1, further comprising:
   a drug library editor workspace comprising a first dedicated user interface configured to receive drug library parameters from a pharmacist; and
   a release workspace comprising a second dedicated user interface configured to release the drug library in the selected second format to the patient device.

5. The compiler system of claim 4, wherein the drug library editor workspace comprises a first dedicated database and first defined entry and exit criteria for a user, wherein the release workspace comprises a second dedicated database and second defined entry and exit criteria for a user.

6. The compiler system of claim 5, wherein the release workspace is configured to generate a release report based on the drug library in the selected second format and to receive a sign-off authorization via the second dedicated user interface from the user.

7. The compiler system of claim 6, wherein the release workspace is configured to store and release the drug library in the selected second format in a read-only format if a sign-off authorization has been received.

8. The compiler system of claim 1, wherein the processing circuit is configured to translate the drug library in the first format to a plurality of different second formats using different patient device-type compiler programs for different respective patient device types.

9. The compiler system of claim 1, further comprising a linker configured to link a plurality of drug libraries into a binary data set for the type of patient device identified.

10. The compiler system of claim 1, wherein the patient devices are clinician-programmable infusion pumps, wherein the drug library comprises hard and soft limits for parameters to be programmed by a clinician.

11. A method of providing a drug library to patient devices, comprising:
  storing a drug library in a first format, the drug library comprising drug data to be used by software on the patient devices to program the patient devices to administer a drug to a patient according to a protocol determined at least in part by a user;
  reading the drug library;
  identifying a type of patient device from a plurality of locally prestored patient device types and prompting the user to load a new compiler program when a patient device type is not recognized among the plurality of locally prestored patient device types;
  receiving the new compiler program for a new patient device type and storing the new compiler program with a plurality of locally prestored compiler programs,
  selecting a compiler program from the plurality of locally prestored compiler programs, each locally prestored compiler program configured to compile the drug library from the first format into a respective second format, each second format being different for each type of patient device;
  using the compiler program selected to translate the drug library from the first format into a selected second format within a healthcare facility;
  storing the drug library in the selected second format; and
  distributing the drug library in the selected second format to a patient device of the type identified.

12. The method of claim 11, wherein the first format is a source code format and the selected second format is a machine code format.

13. The method of claim 11, further comprising:
  receiving drug library parameters from a pharmacist via a first dedicated user interface of a drug library editor; and
  releasing the drug library in the selected second format to the patient device via a second dedicated user interface.

14. The method of claim 13, further comprising using the second dedicated interface to generate a release report based on the drug library in the selected second format and to receive a sign-off authorization from the user.

15. The method of claim 14, further comprising storing and releasing the drug library in the selected second format in a read-only format if a sign-off authorization has been received from the user.

16. The method of claim 11, further comprising translating the drug library in the first format to a plurality of different second formats using different patient device-type compiler programs for different respective patient device types.

17. The method of claim 11, further comprising linking a plurality of drug libraries into a binary data set for the type of patient device identified.

18. The method of claim 11, wherein the patient devices are clinician-programmable infusion pumps, wherein the data set comprises hard and soft limits for parameters to be programmed by a clinician.

19. A computer system for providing a drug library to infusion pumps, comprising:
  a compiler circuit comprising:
    a memory configured to store a drug library in a source code format, the drug library comprising drug data to be used by software already programmed on the infusion pumps to program the infusion pumps to administer a drug to a patient according to a protocol determined at least in part by a clinician, wherein the drug library comprises hard and soft limits for parameters to be programmed by the clinician; and
    a processing circuit disposed within a healthcare facility and configured to:
      identify a type of infusion pump from a plurality of locally prestored infusion pump types and prompt the clinician to load a new compiler program when an infusion pump type is not recognized among the plurality of locally prestored infusion pump types;
      receive the new compiler program for a new infusion pump type and store the new compiler program with a plurality of locally prestored compiler programs:
      select a compiler program from the plurality of locally prestored compiler programs, each locally prestored compiler program configured to compile the drug library from the source code format into a respective machine code format, each machine code format being different for each type of infusion pump;
      use the complier program selected to translate the drug library from the source code format into a selected machine code format;
      store the drug library in the selected machine code format; and
      distribute the drug library in the selected machine code format to a patient device of the type identified;
  a drug library editor circuit comprising a first dedicated user interface configured to receive drug library parameters from a pharmacist; and
  a release circuit comprising a second dedicated user interface configured to release the translated drug library in the second format to the infusion pump of the identified type.

* * * * *